US012778390B2

(12) United States Patent
Dhanotiya et al.

(10) Patent No.: US 12,778,390 B2
(45) Date of Patent: Nov. 3, 2026

(54) MEDICAL DEVICE ACTUATORS AND RELATED METHODS

(71) Applicants: Boston Scientific Scimed, Inc., Maple Grove, MN (US); Boston Scientific Medical Device Limited, Galway (IE)

(72) Inventors: Aditya Dhanotiya, Indore (IN); Nabarun Bhowmick, Kolkata (IN); James Weldon, Newton, MA (US); Shrikant Vasant Raut, Mumbai (IN); Subodh Morey, Ponda (IN)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 658 days.

(21) Appl. No.: 18/162,221

(22) Filed: Jan. 31, 2023

(65) Prior Publication Data

US 2023/0248218 A1 Aug. 10, 2023

Related U.S. Application Data

(60) Provisional application No. 63/307,785, filed on Feb. 8, 2022.

(51) Int. Cl.
*A61B 1/00* (2006.01)
*A61B 1/273* (2006.01)

(52) U.S. Cl.
CPC ...... *A61B 1/00128* (2013.01); *A61B 1/00133* (2013.01); *A61B 1/2736* (2013.01)

(58) Field of Classification Search
CPC ........... A61B 1/00128; A61B 1/00133; A61B 1/2736; A61B 1/00066; A61B 1/00098; A61B 1/00042; A61B 1/0052
See application file for complete search history.

(56) References Cited

U.S. PATENT DOCUMENTS 5,318,526 A * 6/1994 Cohen .................. A61B 1/0055 604/95.04
2013/0205937 A1* 8/2013 Arai .................. G02B 23/2476 74/527

(Continued)

OTHER PUBLICATIONS

Cappell, M. S., "Colonoscopist's thumb: DeQuervains's syndrome (tenosynovitis of the left thumb) associated with overuse during endoscopy," Gastrointestinal Endoscopy, vol. 64, pp. 841-843 (2006).

(Continued)

*Primary Examiner* — William J Levicky
*Assistant Examiner* — Olivia Walker
(74) *Attorney, Agent, or Firm* — Bookoff McAndrews, PLLC

(57) ABSTRACT

A linkage assembly for a medical device, may comprise a control lever, a rotatable member rotatable about a first axis, and a plurality of linkages including a first linkage, a second linkage, and a third linkage. The first linkage may include a first end coupled to the rotatable member and a second, opposite end coupled to a first end of the second linkage. The second linkage may include the first end coupled to the second end of the first linkage and a second, opposite end coupled to a first end of the third linkage, wherein the second linkage may be rotatable about a second axis parallel with the first axis. A second end of the third linkage may translate along a third axis, and the second axis is offset from the third axis.

18 Claims, 9 Drawing Sheets

(56) References Cited

U.S. PATENT DOCUMENTS

| | | | |
|---|---|---|---|
| 2015/0148598 A1 | 5/2015 | Fukushima et al. | |
| 2016/0089003 A1 | 3/2016 | Morimoto et al. | |
| 2016/0089125 A1* | 3/2016 | Morimoto .......... | A61B 1/00098 600/107 |
| 2018/0092512 A1 | 4/2018 | Hiraoka et al. | |
| 2020/0214544 A1* | 7/2020 | Harada .................. | A61B 1/018 |
| 2022/0175480 A1* | 6/2022 | Oliver .................... | B25J 18/007 |
| 2022/0202280 A1 | 6/2022 | Powell et al. | |

OTHER PUBLICATIONS

Villa, E. et al., “Endoscopy-related musculoskeletal injuries in gastroenterology fellows,” Endoscopy International Open, vol. 7, pp. E808-E812 (2019).

International Search Report and Written Opinion issued in International Application No. PCT/US2023/061654, issued Apr. 28, 2023 (12 pages).

* cited by examiner

MEDICAL DEVICE ACTUATORS AND RELATED METHODS

CROSS-REFERENCE TO RELATED APPLICATIONS

This application claims the benefit of priority under 35 U.S.C. § 119 from U.S. Provisional Application No. 63/307,785, filed Feb. 8, 2022, which is incorporated by reference herein in its entirety.

TECHNICAL FIELD

Various aspects of this disclosure relate generally to devices and methods for actuators of medical devices, and in particular, to actuators for components of duodenoscopes, such as elevator levers.

BACKGROUND

Duodenoscopes may include a handle and a sheath insertable into a body lumen of a subject. The sheath may terminate in a distal tip portion, which may include features such as optical elements (e.g., camera, lighting), air/water outlets, and working channel openings. An elevator may be disposed at a distal tip and may be actuatable in order to change an orientation of a medical device/tool passed through the working channel. For example, the elevator may be pivotable or otherwise movable.

Elements/actuators in the handle may control the elements of the distal tip. For example, buttons, knobs, levers, etc. may control elements of the distal tip. The elevator may be controlled via a control mechanism in a handle, such as a lever, which may be attached to a control wire that attaches to the elevator. When a mechanism (e.g., a lever) is activated, the wire may move proximally and/or distally, thereby raising and/or lowering the elevator. Activating such a mechanism (e.g., lever/actuator) may require an operator to exert a large amount of force in some configurations, and maintain such force for extended periods of time. Indeed, a variety of procedures may require constant and repetitive operation of the lever throughout the procedure, such as rapidly raising and lowering the elevator or holding the elevator in a desired position. Repetitive activity, static muscle loading, and awkward body movement posture may result in musculoskeletal problems of physicians and other medical personnel. Therefore, it may be desirable to decrease the amount of force required to raise and/or lower the elevator in order to enable an operator to perform a medical procedure more comfortably, accurately, and for longer periods of time.

The devices, and methods of this disclosure may rectify one or more of the deficiencies described above or address other aspects of the art.

SUMMARY

Each of the aspects disclosed herein may include one or more of the features described in connection with any of the other disclosed aspects. Examples of the disclosure relate to, among other things, devices and methods for actuating an elevator on a distal end. However, it may be understood by those knowledgeable in the art that the mechanisms provided here may be used to articulate, rotate, or otherwise manipulate a distal end of a device other than an elevator.

In one example, a linkage assembly for a medical device may comprise a control lever, a rotatable member rotatable about a first axis, and a plurality of linkages including a first linkage, a second linkage, and a third linkage. The first linkage includes a first end coupled to the rotatable member and a second, opposite end coupled to a first end of the second linkage, and the second linkage includes the first end coupled to the second end of the first linkage and a second, opposite end coupled to a first end of the third linkage, wherein the second linkage is rotatable about a second axis parallel with the first axis. A second end of the third linkage may translate along a third axis, and the second axis is offset from the third axis.

Any example of a linkage assembly described herein may further include a slider having a longitudinal axis. The slider may be coupled to a second end of the third linkage. The linkage assembly may be configured such that the second linkage extends perpendicular to the longitudinal axis of the slider, and the first end of the second linkage is a right-hand end of the second linkage when viewed from above. In a configuration in which the second linkage extends perpendicular to the longitudinal axis of the slider, the first end of the second linkage is a left-hand end of the second linkage when viewed from above. The slider is operatively coupled to a control member extending distally to a distal member. The distal member may be, for example, an elevator of the medical device. Manipulation of the control lever is configured to result in manipulation of the elevator so as to adjust an orientation of a tool extending through the elevator. In some embodiments, at least one of the plurality of linkages is curved. The second linkage pivots about a fixed protrusion extending along the second axis. The second linkage may be eccentrically mounted to the fixed protrusion such that a first length of the second linkage extending from the first end of the second linkage to the fixed protrusion is different than a second length of the second linkage extending from the fixed protrusion to the second end of the second linkage. In any example, the first linkage may be coupled to an intermediary component, wherein the intermediary component is coupled to the rotatable member. In any example, the plurality of linkages are configured in a Z-formation.

In another example, the linkage assembly may include a slider having a longitudinal axis, wherein the slider is connected to a second end of the third linkage, and wherein the fixed protrusion is offset from the longitudinal axis of the slider.

The control lever, rotatable member, and first linkage form a second-class lever assembly, and the first linkage, second linkage, and third linkage form a first-class lever assembly. Additionally or alternatively, in any example, a proximal portion of the control member may further comprise a hypotube.

In another example, a linkage assembly for a medical device may comprise a rotatable member configured to rotate about a first rotational axis, a slider movable along a range of motion extending from a most retracted position of the slider to a maximum advancement of the slider, and a series of elevator linkages rotatably coupled to the rotatable member at a first end of the series and rotatably coupled to the slider on a second end of the series. At least one elevator linkage of the series of elevator linkages is rotatable about a second rotational axis different than the first rotational axis, and movement of the slider along the range of motion results in movement of a distal member coupled to the slider via a control member. A proximal portion of the control member further comprises a hypotube. The distal member is an elevator of the medical device. The second rotational axis may be perpendicular to a longitudinal axis extending longitudinally through the slider.

In another example, a linkage assembly for a medical device may comprise: a rotatable member configured to rotate about a rotation axis, a slider, a plurality of elevator linkages, and an elevator assembly. The plurality of elevator linkages may form a plurality of levers to manipulate the elevator assembly. The plurality of levers include (i) a second-class lever and (ii) a first-class lever connected to the second class lever, and the elevator assembly may be connected to the first-class lever.

It may also be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects this disclosure and together with the description, serve to explain the principles of the disclosure.

DETAILED DESCRIPTION

Aspects of this disclosure include devices and methods for actuators of medical devices, and in particular to actuators for components of duodenoscopes, such as elevator levers. The ability to manipulate a distal component of a scope, such as an elevator, can, for example, alleviate user discomfort associated with exerting a large amount of force to activate the actuator.

Examples of the disclosure may relate to devices and methods of activating, deactivating, or otherwise manipulating an elevator of a duodenoscope or a portion of a distal end of a device (e.g., a scope). Various examples described herein include a series of first- and second-class levers utilized to reduce the force required to activate or deactivate the elevator. The reduction of force may be related and/or equivalent to a reduction of torque. Reference will now be made in detail to examples of the disclosure described above and illustrated in the accompanying drawings. Wherever possible, the same reference numbers will be used throughout the drawings to refer to the same or like parts.

The lever assemblies described below are described as being used to raise/lower an elevator of a duodenoscope. Although side-facing devices are particularly discussed, the embodiments described herein may also be used with front-facing endoscopes (e.g., endoscopes where a viewing element faces longitudinally forward). Additionally, it will be appreciated that the lever assemblies described herein may have a wider application. For example, the lever assembly may also be used to control other medical device components (e.g., steering or braking components). It will also be appreciated that other devices may include an elevator or any other distal component requiring activation or movement for which these assemblies can be used. Other devices include, but are not limited to, sheaths, catheters, scopes, or any other suitable delivery device or medical device that may include one or more distal components requiring actuation or movement. This may also include non-medical devices, such as borescopes. Thus, the following descriptions and illustrations should be considered illustrative in nature and not limiting the scope of this disclosure.

Figure 1A:
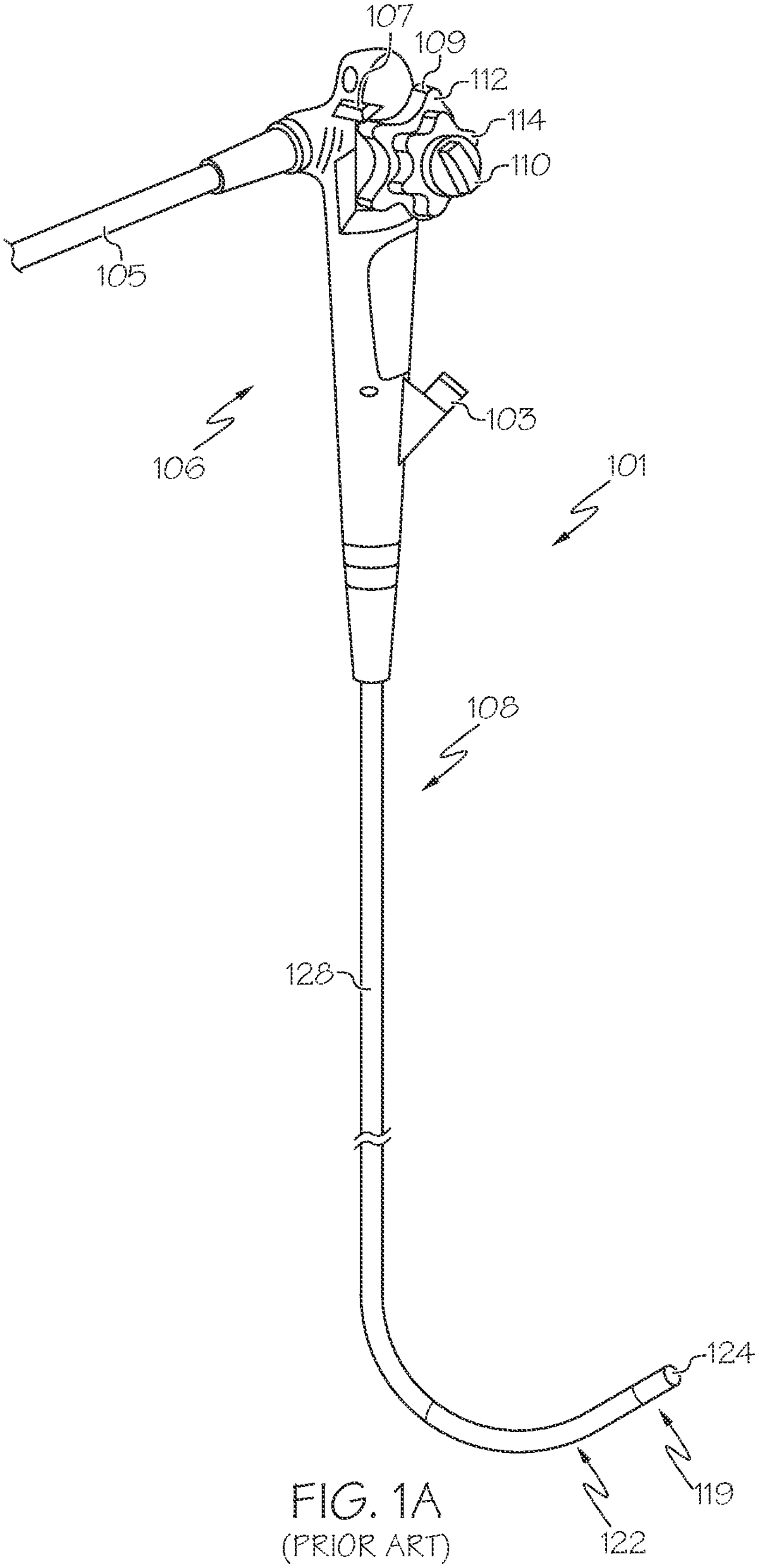
FIG. 1A (PRIOR ART)
FIGS. 1A and 1B depict an exemplary duodenoscope, according to aspects of this disclosure.
Figure 1B:
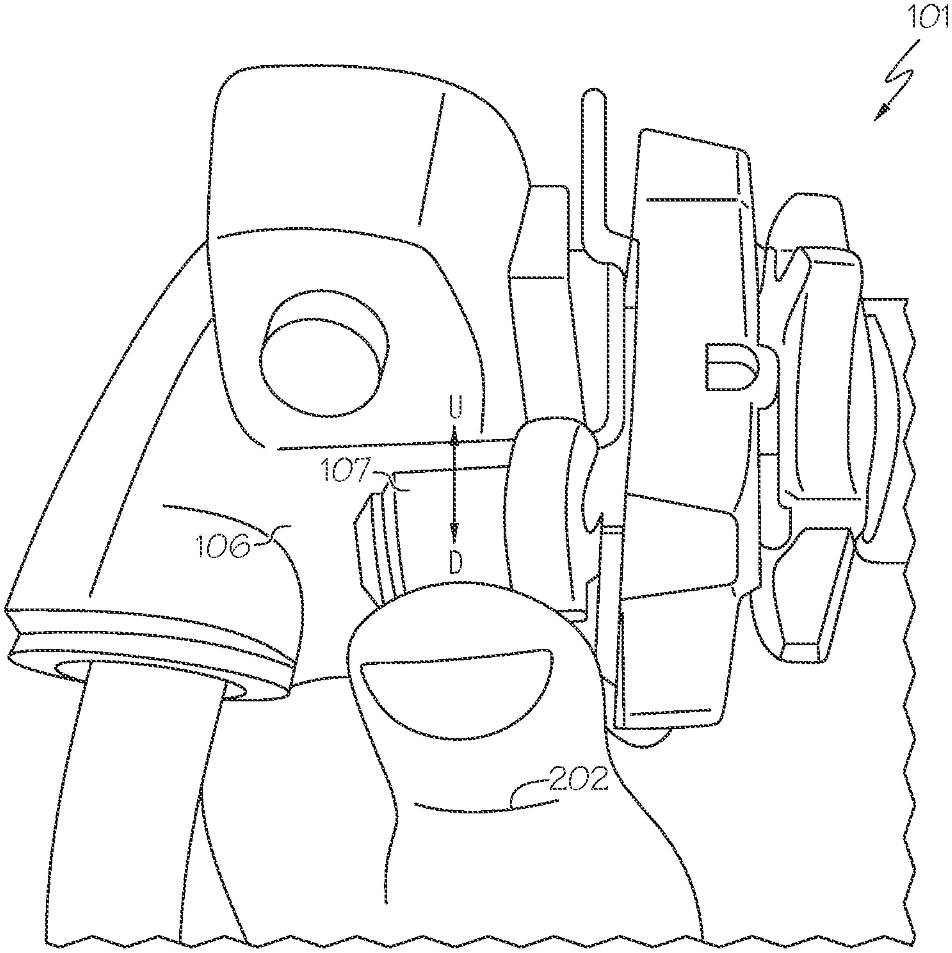
FIG. 1B (PRIOR ART)

FIG. 1A illustrates an exemplary duodenoscope 101, and FIG. 1B illustrates a user gripping duodenoscope 101. Duodenoscope 101 comprises a handle 106 and an insertion portion 108. Duodenoscope 101 may also include an umbilicus 105 for purposes of connecting duodenoscope 101 to sources of, for example, air, water, suction, power, etc., as well as to image processing and/or viewing equipment (not shown).

Insertion portion 108 may include a sheath or shaft 128 and a distal tip 119. Distal tip 119 may include an imaging device (e.g., a camera) and a lighting source (e.g., an LED or an optical fiber) (not shown). Distal tip 119 may be side-facing. That is, the imaging device and lighting source may face radially outward, perpendicularly, approximately perpendicularly, or otherwise transverse to a longitudinal axis of shaft 128 and/or distal tip 119.

Distal tip 119 may also include an elevator 124 for changing an orientation of a tool inserted in a working channel of duodenoscope 101. The mechanisms to activate (e.g., raise) or de-activate (e.g., lower) elevator 124 are to be described in further detail below. Additionally, elevator 124 may alternatively be referred to as a swing stand, pivot stand, raising base, or any suitable other term. Elevator 124 may be pivotable via, e.g., an actuation wire or another control element that extends from handle 106, through shaft 128, to elevator 124.

A distal portion of shaft 128 that is adjacent and/or connected to distal tip 119 may have a steerable section 122. Steerable section 122 may be, for example, an articulation joint. Shaft 128 and steerable section 122 may include a variety of structures that are known or may become known in the art.

Handle 106 may have one or more actuators/control mechanisms 112, 114. Control mechanisms 112, 114 may enable deflection/steering of steerable section 122 and thereby, distal tip 119. For example, control mechanisms (e.g., knobs) 112, 114 may control movement of distal tip 119 in left, right, up, and/or down directions. That is, a first control mechanism 112 may control deflection of distal tip 119 along a first plane (e.g., up, down); while a second control mechanism 114 may control deflection of distal tip 119 along a second plane (e.g., left, right). The second plane may be orthogonal, perpendicular, and/or transverse to the first plane. Handle 106 may further include one or more locking mechanisms 109, 110 (e.g., knobs or levers) for securing a position of control mechanisms 112, 114. When engaged or actuated, locking mechanism(s) 109, 110 may prevent manipulation (e.g., rotation) of control mechanisms 112, 114 thereby preventing deflection/steering of steerable section 122 or distal tip 119 in at least one of an up, down, left, or right direction. Further, handle 106 may include an elevator control lever 107 (interchangeably referred to herein as "control lever", "lever," or "elevator lever"). Manipulation of elevator control lever 107 may result in movement of elevator 124. For example, manipulation of elevator control lever 107 may raise and/or lower elevator 124, as will be described further herein. Further, a port 103 may allow passage of a tool into a working channel of duodenoscope 101 through shaft 128 to distal tip 119.

FIG. 1B depicts a user gripping handle 106 of duodenoscope 101. Specifically, a user 202 places a thumb or finger on lever 107 to manipulate elevator 124. The user 202 may push, press, or otherwise urge lever 107 up (e.g., in direction U) to activate elevator 124. Similarly, user 202 may pull, press, or otherwise urge lever 107 down (e.g., in direction D) to de-activate elevator 124, or vice-versa. Activating or de-activating elevator 124 may include adjusting an angle of the elevator 124 in at least a first direction and a second direction. Although the depicted lever 107 is arranged such that the user 202 manipulates lever 107 with their thumb, it may be understood by one knowledgeable in the art that this configuration is not limited. For example, lever 107 may be configured/positioned such that a user may utilize other fingers to manipulate lever 107.

In use, an operator may insert insertion portion 108 into a body lumen of a subject and navigate distal tip 119 to a procedure site in the body lumen. The operator may insert a tool (not shown) into port 103, and pass the tool through a working channel of shaft 128 toward distal tip 119. The tool may exit the working channel at distal tip 119. The user may use elevator lever 107 to raise elevator 124 and angle the tool toward a desired location (e.g., a papilla of the pancreatico-biliary tract). Once so positioned, the user may use the tool to perform a medical procedure.

Figure 2:
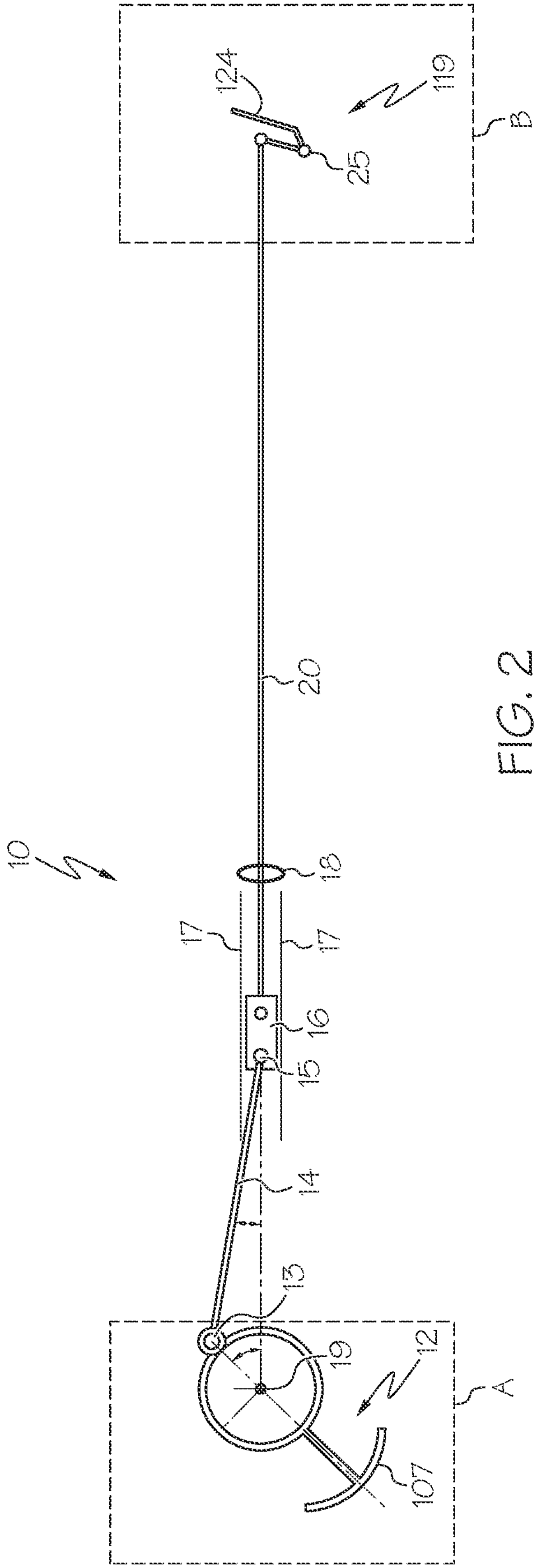
FIG. 2 depicts a view of a single-link lever assembly, including a distal elevator, according to aspects of this disclosure.

FIG. 2 depicts a single-link elevator assembly 10 used with the duodenoscope 101 of FIG. 1A. The assembly may include a rotatable member 12 having a lever 107, described above. The rotatable member 12 may be rotated about axis 19 when the user manipulates lever 107. A proximal portion of an elevator linkage 14 may be rotatably coupled to the rotatable member 12 at a first lever connector 13 such that elevator linkage 14 may move relative to rotatable member 12, or vice versa. The first lever connector 13 may be positioned on an opposite side of rotatable member 12 from lever 107. A slider 16 may be rotatably coupled to a distal portion of elevator linkage 14 at a second lever connector 15 such that elevator linkage 14 may move relative to slider 16, or vice versa. For example, when the user rotates rotatable member 12 via lever 107, elevator linkage 14 is moved proximally or distally, causing the slider 16 to move proximally or distally within a track 17. For example, slider 16 may be movable within track 17, for example, from a most proximal, or retracted, position within track 17 to a distal, or maximally advanced, position within track 17. A proximal end of a control wire 20 may be fixedly or removably coupled to a distal end of the slider 16 by means of a crimp, set screw, glue, or any other securing structure commonly known in the art. Alternatively, a proximal end of the control wire 20 may extend through a proximal end of slider 16. Control wire 20 may be held in place by a crimp, set screw, glue, or any other means commonly known in the art. The proximal end (or any other portion) of the control wire 20 may also be comprised of a hypotube (not pictured) in order to provide additional structural (e.g., columnar) support to the control wire 20. The control wire 20 may also extend through a Bowden cable (not pictured) within the shaft and to provide additional structural support within shaft 128 of FIG. 1A. The Bowden cable may extend into a portion of handle 106 to provide structural support, as well. As shown in FIG. 2, control wire 20 may extend through an O-ring 18. O-ring 18 may be used to contain or otherwise control wire 20 within the handle 106, shown in FIG. 1A. Additionally, a small amount of friction may be generated between O-ring 18 and control wire 20 to provide the user with more precise movement of an elevator 124 located at a distal tip 119. For example, O-ring 18 may prevent the control wire from recoiling or returning to an undesired position when lever 107 is released by the user.

As previously described, distal tip 119 may include elevator 124, which may be used for changing an orientation of a tool (not pictured) inserted in a working channel (not pictured) of duodenoscope 101. Elevator 124 may alternatively be referred to as a swing stand, pivot stand, raising base, or any suitable other term. Elevator 124 may be pivotable about pivot point 25 via, e.g., control wire 20 or another control element that extends from a proximal portion of the elevator assembly 10 within handle 106 of FIG. 1A, and to elevator 124.

The previously described assembly can be categorized as a series of first-class levers (e.g., levers having the fulcrum between the force and the load). A first lever in the series is depicted within box A (referred to as first lever A) and a second lever is depicted within box B of FIG. 2 (referred to as second lever B). First lever A receives a user-applied force at lever 107 so as to rotate rotatable member 12 about axis 19. That is, axis 19 is the fulcrum of first lever A. Rotating lever 107 about axis 19 results in the movement of elevator linkage 14 about first lever connector 13. In other words, elevator linkage 14 is the load of first lever A. The remaining intermediate components (e.g., slider 16, O-ring 18, and control wire 20) couple first lever A with second lever B. When lever 107 is rotated about axis 19, slider 16 is translated within track 17. Track 17 may define the range of which slider 16 extends proximally or distally. Lengthening track 17 will result in an increased range for which slider 16 may travel, while shortening track 17 will result in a decreased range for which slider 16 may travel. Because control wire 20 is coupled to slider 16, this movement results in the translation of control wire 20 within shaft 128 of duodenoscope 101. Thus, control wire 20 applies a load to elevator 124 so as to rotate elevator 124 about pivot point 25. In other words, elevator 124 is the load of the second lever B while pivot point 25 is the fulcrum of the second lever B. This motion activates or de-activates the elevator 124.

While the combination of two first-class levers provides a significant mechanical advantage to activate or de-activate elevator 124, the remaining figures demonstrate improvements to further increase the mechanical advantage associated with rotating lever 107 about axis 19.

Figure 3A:
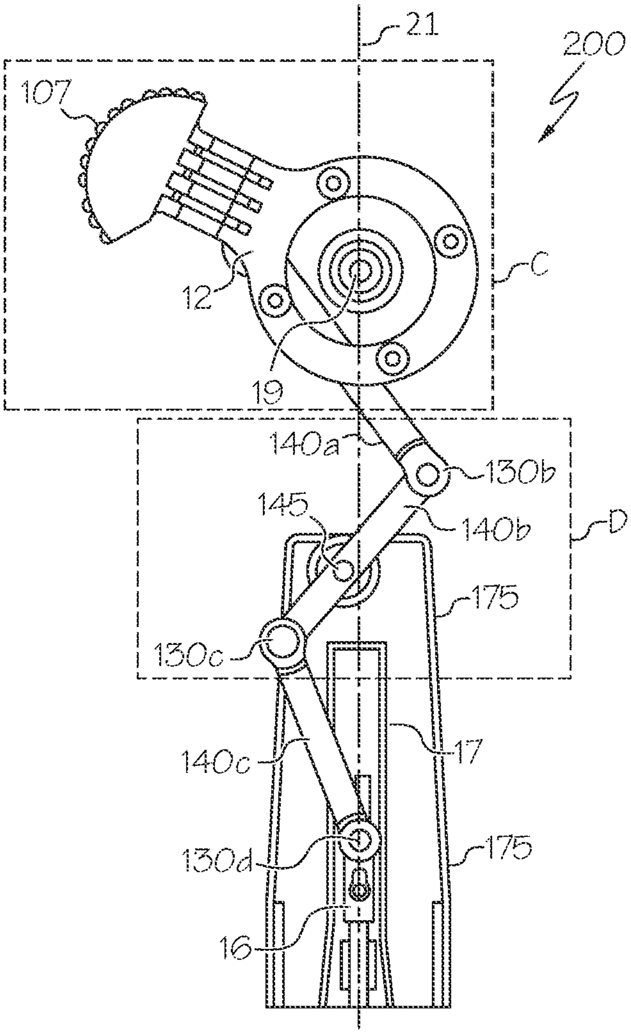
FIGS. 3A-3D illustrate an exemplary multi-link lever assembly, according to aspects of this disclosure.
Figure 3B:
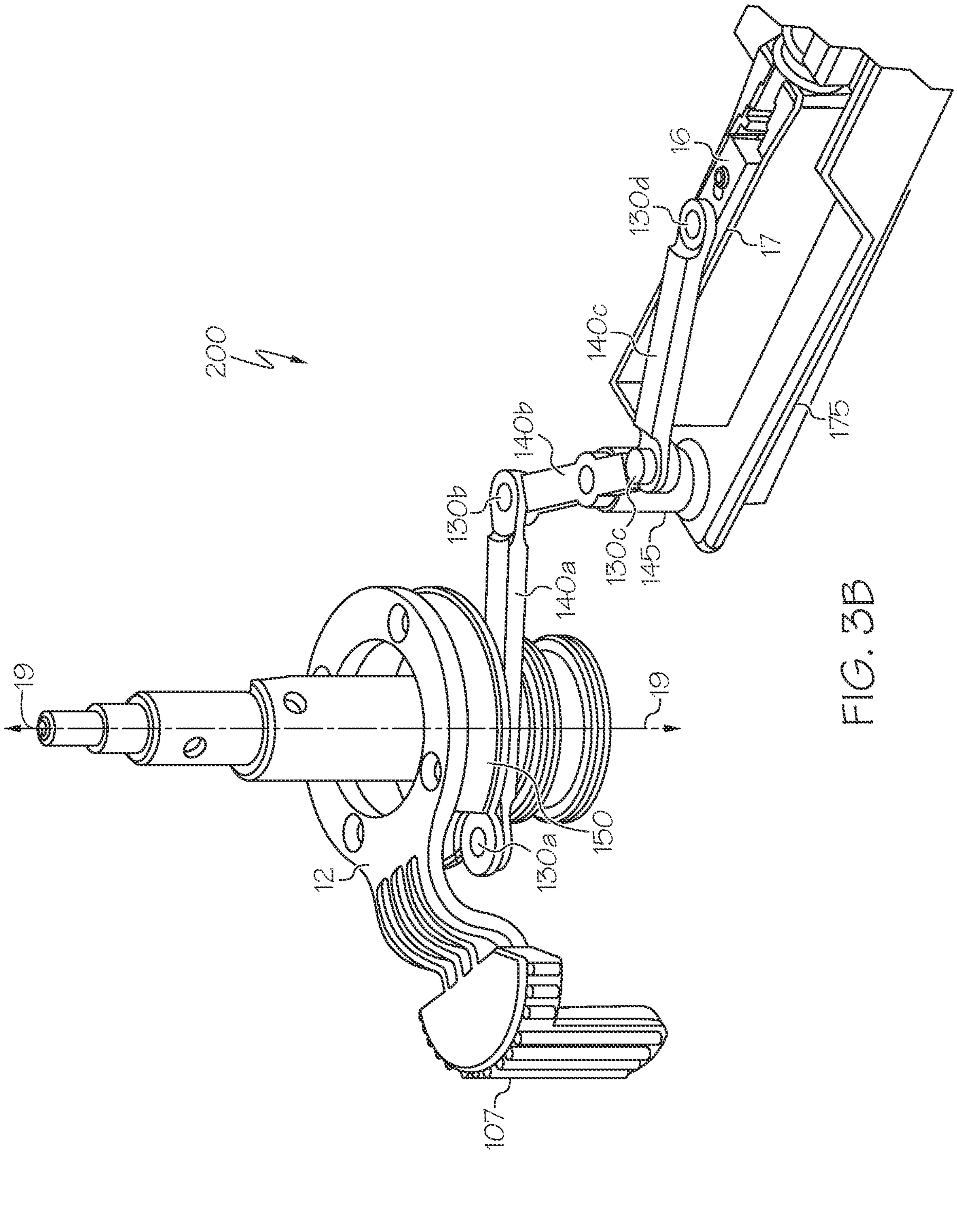
Figure 3C:
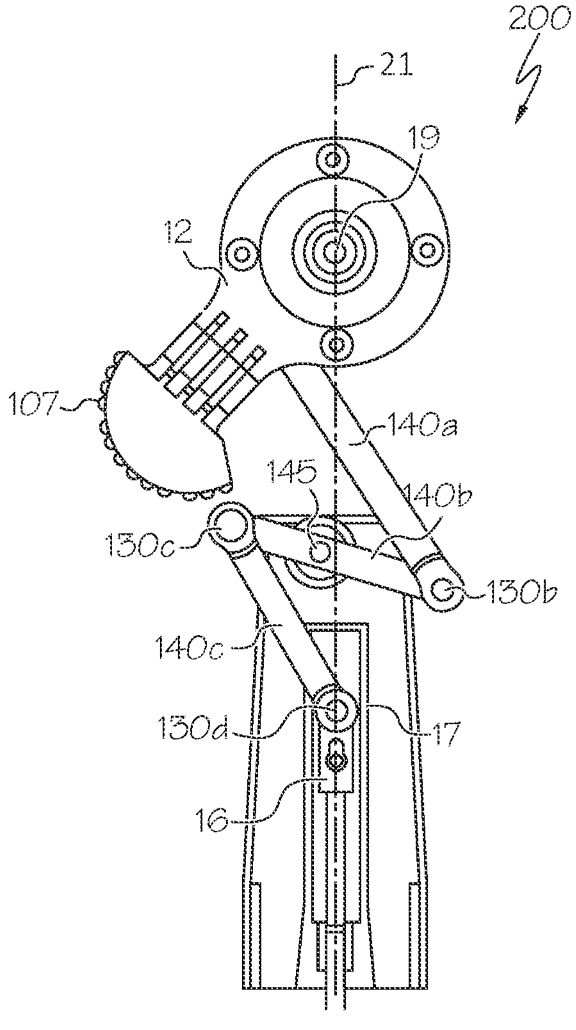
Figure 3D:
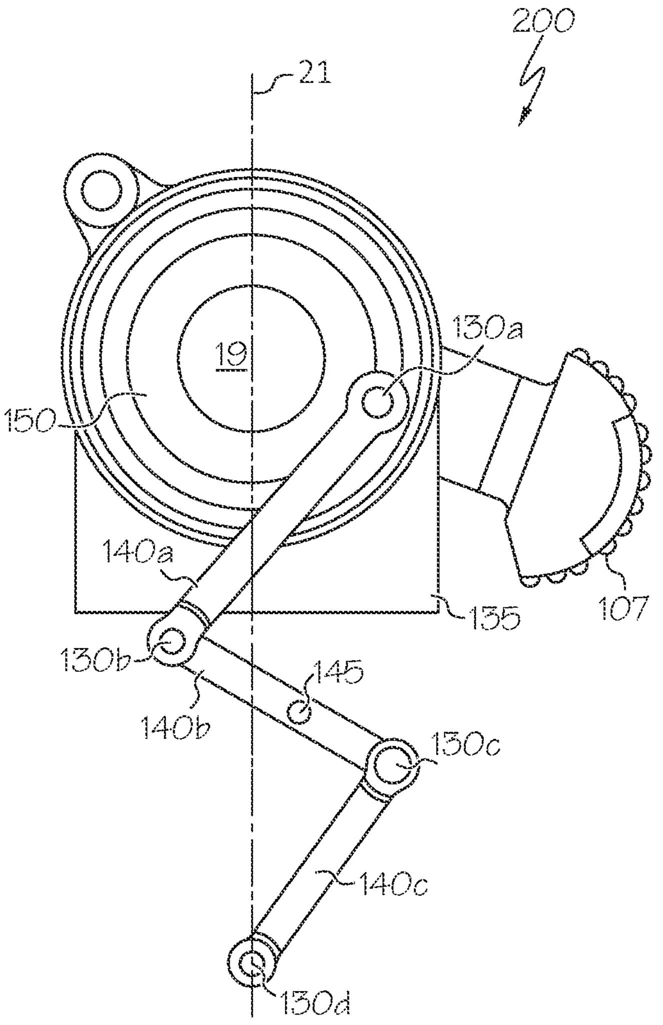

FIGS. 3A-3D depict an exemplary elevator lever assembly 200 for use with duodenoscope 101, where the same elements are referred to with the same reference numbers previously described. This embodiment utilizes a series of first- and second-class levers (e.g., levers in which the load is between the effort (force) and the fulcrum) to provide functionality to elevator 124 of FIG. 2. This may be accomplished through rotation of rotatable member 12 via lever 107. FIGS. 3A and 3B show exemplary elevator lever assembly 200 in a first configuration (FIG. 3A, 3B) and in a second configuration (FIG. 3C). The first configuration (FIG. 3A, 3B) may correspond to an elevator being in a lowered (e.g., open) position. The second configuration (FIG. 3C) may correspond to an elevator being in a raised (e.g., closed) position. However, these configurations are not limited, as a user may require elevator 124 to be raised or lowered multiple times throughout a procedure, and to varying degrees. FIG. 3D depicts an alternative view of the subassembly, in the second configuration, from the bottom, and includes additional components, such as a handle piece 135. Handle piece 135 may be utilized to secure the linkage assembly to the handle 106 of FIG. 1. Handle piece 135 may be various shapes and sizes and may be secured to handle 106 by a variety of means commonly known in the art. This may include the use of screws or other fasteners, glue, a snap-fit, or any other method commonly known in the art.

Referring to FIGS. 3A and 3B, rotatable member 12 may be rotated about axis 19 via lever 107. Axis 19 may be in line with and perpendicular to a center longitudinal axis 21, to be described further herein. A proximal face of lever 107 may include ridges, bumps, indentations, etc., to further facilitate a user's grip on lever 107. The proximal face may be curved or otherwise configured to provide leverage and comfort to the user, as well. Alternatively, the proximal face of lever 107 may be textured, smooth, and/or cushioned to facilitate a more comfortable grip for the user. Rotatable member 12 may be rotated about axis 19 when lever 107 is manipulated by the user. A proximal portion of a first elevator linkage 140*a* may be rotatably coupled to rotatable member 12 at a first lever connector 130*a* (shown in FIGS. 3B, 3D) by means of a pin, clip, screw, or other means commonly known in the art. However, in some embodiments, rotatable member 12 may be coupled to one or more intermediary components 150, as shown in FIGS. 3B and 3D. One or more intermediary components 150 may also be rotatable about axis 19 with rotatable member 12. Thus, first lever connector 130*a* may alternatively be coupled to one or more intermediary components 150. However, regardless of whether first lever connector 130*a* is directly coupled to rotatable member 12 or to one or more intermediary components 150, first lever connector 130*a* is positioned between lever 107 and axis 19. This placement creates a second-class lever, to be described in further detail below.

A distal portion of first elevator linkage 140*a* may be rotatably coupled to a second elevator linkage 140*b* by means of a second lever connector 130*b*. This connection may be accomplished through the same or similar means described above with respect to first lever connector 130*a*. However, second elevator linkage 140*b* pivots about a protrusion 145 extending from a proximal portion of a slider track 175. Protrusion 145 may be offset from the center longitudinal axis 21 of the slider track 175, forming a third axis. The center longitudinal axis 21 may extend through a center of slider track 175 and parallel to a center axis of the handle. Slider track 175 may be a separable component relative to handle 106, or it may be molded as a portion of handle 106. Slider track 175 may further comprise track 17, described above, and may be a variety of shapes and sizes. Protrusion 145 may extend partially or completely through second elevator linkage 140*b*. To maximize the mechanical advantage of this configuration, protrusion 145 may be configured to be at approximately two-thirds of a length of the second elevator linkage 140*b*. For example, for an elevator linkage 140*b* approximately 25 mm in length, second elevator linkage 140*b* may pivot about the protrusion 145 at approximately 14.5 mm from a proximal end of second elevator linkage 140*b*. The remaining third, or 10.5 mm, of the length of second elevator linkage 140*b* may extend past the protrusion 145 and may be rotatably coupled to a proximal end of a third elevator linkage 140*c* via a third lever connector 130*c*. Second elevator linkage 140*b* may be rotatably coupled to protrusion 145 by, for example, a snap-fit, a clip, or other means commonly known in the art. In other words, second elevator linkage 140*b* may be eccentrically mounted to the protrusion 145. In one configuration, second elevator linkage 140*b* may extend perpendicular to the longitudinal axis of the slider, the first end of the second linkage is a right-hand end of the second linkage when viewed from above. A distal end of third elevator linkage 140*c* may be pivotally coupled to a slider 16 via a fourth lever connector 130*d*. The fourth lever connector 130*d* may translate along the third axis offset from the second axis.

In may be understood, however, that the aforementioned measurements are for demonstrative purposes only. Alternative measurements may be utilized to accomplish the desired configuration and/or an improved mechanical advantage of the subassembly.

As shown in FIG. 3A, first elevator linkage 140*a* is rotatably coupled to a first end (e.g., right portion) of the second elevator linkage 140*b*, and third elevator linkage 140*c* is rotatably coupled on a second end (e.g., left portion) of the second elevator linkage 140*b*. The configuration of elevator linkages 140*a*, 140*b*, and 140*c* generally result in a Z-formation, when observing the assembly from above. As previously described with relation to FIG. 2, rotation of lever 107 relative to axis 19 ultimately results in the activation or de-activation of elevator 124 (FIGS. 1A, 1B, 2) at the distal tip 119 of duodenoscope 101. More specifically, urging lever 107 down results in first elevator linkage 140*a* extending distally. In turn, this motion causes the second elevator linkage 140*b* to pivot about protrusion 145, resulting in the proximal translation of third elevator linkage 140*c* and slider 16. Thus, the control wire 20 is pulled proximally and the elevator is activated. The opposite effect may occur if lever 107 is urged in the opposite direction. To capture mechanical advantage, this embodiment utilizes a series of second- and first-class levers.

A first lever in the series is depicted within box C (referred to as first lever C) and a second lever in the series is depicted within box D (referred to as second lever D). First lever C is arranged as a second-class lever. For example, first elevator linkage 140*a* (e.g., the load of first lever C) is between axis 19 (e.g., the fulcrum of first lever C) and lever 107 (e.g., point of force application of first lever C). In other words, the load of first lever C is between the point at which force is applied and the fulcrum. When a force is applied to lever 107, first elevator linkage 140*a* (e.g., the load) is translated relative to axis 19 (e.g., the fulcrum). A distal portion of first elevator linkage 140*a* subsequently applies force on second lever D in the series. Second lever D is arranged as a first-class lever. When first elevator linkage 140*a* is translated, second elevator linkage 140*b* pivots about protrusion 145 (e.g., the fulcrum). In other words, first elevator linkage 140*a* applies the force necessary to translate the remaining components on an opposite side of second elevator linkage 140*b* (e.g., the load) about protrusion 145 (e.g., the fulcrum). That is, the fulcrum of the second lever D is between the point at which force is applied and the location of the load. The combination of these levers (e.g., a second class lever (first lever C) followed by a first class lever (second lever D)) requires less force to activate or de-activate elevator 124 of the distal tip 119.

The measurements of elevator linkages 140*a*, 140*b*, 140*c* may differ slightly, as well, in order to maximize the mechanical advantage of the subassembly or fit within a handle. For example, a distance extending from a surface of lever 107 (e.g., where the user would apply force) to axis 19 may be about 33 mm. The proximal portion of elevator linkage 140*a* may be rotatably fixed about 13 mm from axis 19 and between lever 107. Additionally, the length of elevator linkage 140*a* may be about 32 mm, the length of second elevator linkage 140*b* may be about 25 mm in length, and third elevator linkage 140*c* may be about 24 mm in length. In this configuration, second elevator linkage 140*b* may extend perpendicular to the longitudinal axis of the slider, the first end of the second linkage is a left-hand end of the second linkage when viewed from above. The aforementioned exemplary lengths may accomplish a mechanical advantage of 2.5 within box C and a mechanical advantage of 1.4 within box D. It may also be understood that other lengths for the elevator lever 107 and one or more of the elevator linkages 140*a*, 140*b*, 140*c* may be utilized to accomplish a desired mechanical advantage or configuration or be otherwise manipulated to fit within a handle of a medical device.

Similarly to the method described above with respect to the embodiment of FIG. 2, an operator may insert insertion portion 108 into a body lumen of a subject, and distal tip 119 may be navigated to a procedure site in the body lumen. The operator may insert a tool (not shown) into port 103, and pass the tool through shaft 128 via a working channel to distal tip 119. The tool may exit the working channel at distal tip 119. The user may use elevator control lever 107 to raise elevator 124 and angle the tool toward a desired location (e.g., a papilla of the pancreatico-biliary tract). The user may use the tool to perform a medical procedure.

Figure 4A:
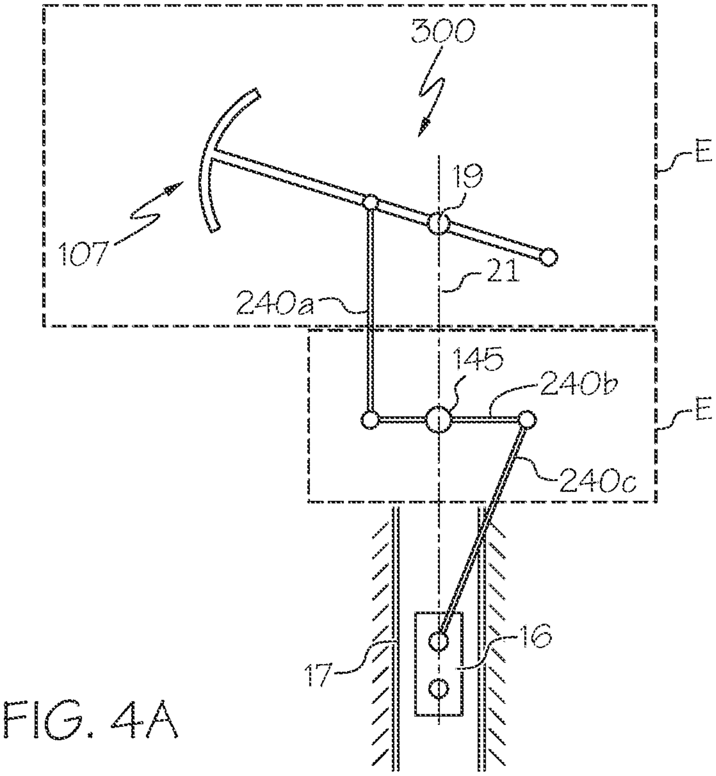
FIGS. 4A-4C illustrate an alternative exemplary multi-link lever assembly, according to aspects of this disclosure.
Figure 4B:
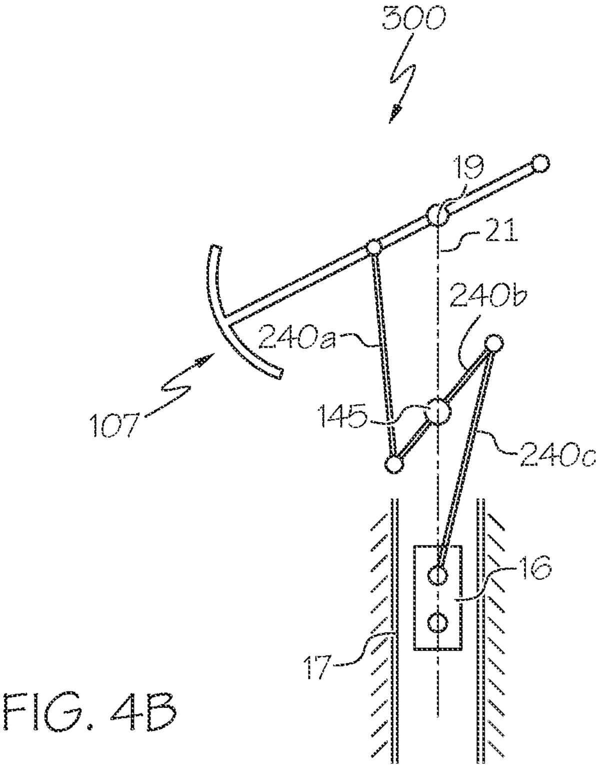
Figure 4C:
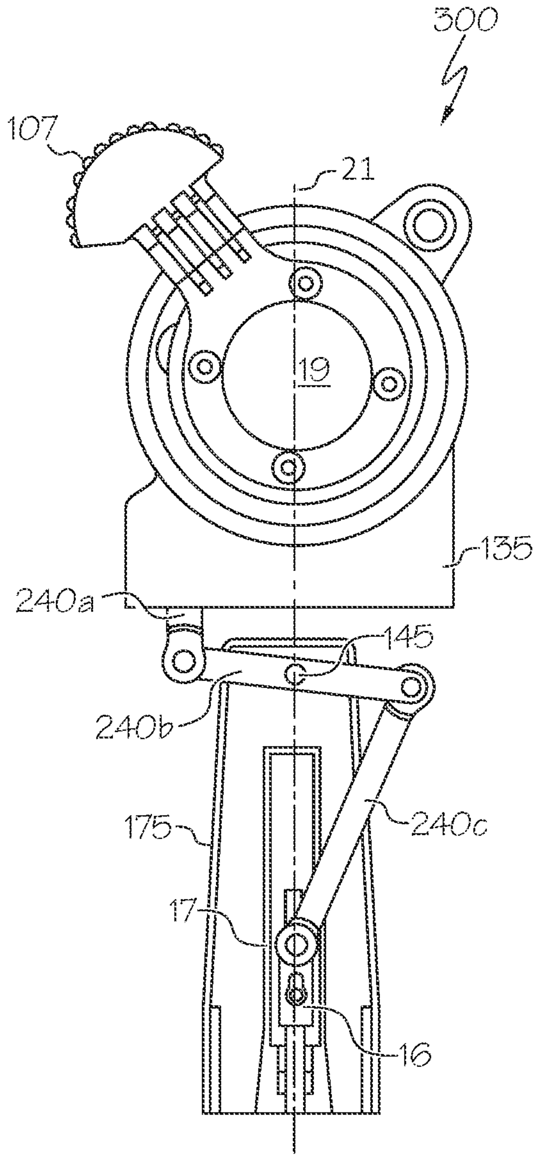

FIGS. 4A-4C depict an alternative exemplary elevator lever assembly 300, where the same elements are referred to with the same reference numbers previously described. The arrangement of FIGS. 4A-4C may operate similarly to the arrangement of FIGS. 3A-3D except for the modifications described herein. The arrangement of FIGS. 4A-4C also utilizes a series of first- and second-class levers, and includes a first elevator linkage 240*a*, a second elevator linkage 240*b*, and a third elevator linkage 240*c*. The configuration of elevator linkages 240*a*, 240*b*, and 240*c* generally result in an S-formation, when observing the assembly from above. However, the orientation of elevator linkages 240*a* and 240*c* relative to second elevator linkage 240*b* and the placement of protrusion 145 relative to center longitudinal axis 21 of slider track 175 differs slightly than the arrangement of FIGS. 3A-3D. Specifically, first elevator linkage 240*a* is rotatably coupled to a first end (e.g., left portion) of the second elevator linkage 240*b*, and third elevator linkage 240*c* is rotatably coupled on a second end (e.g., right portion) of the second elevator linkage 240*b*. A first lever in the series is depicted within box E (referred to as first lever E) and a second lever in the series is depicted within box F (referred to as second lever F). As shown, first lever E in the series is arranged as a second-class lever because first elevator linkage 240*a* (e.g., load) is positioned between axis 19 (e.g., fulcrum) and lever 107 (e.g., the point of application of a force). Also, second lever F is arranged as a first-class lever because third elevator linkage 240*c* (e.g., the load) and first elevator linkage 240*a* (e.g., the point of application of a force) are on opposite sides of the protrusion 145 (e.g., fulcrum). Thus, when lever 107 is translated downwards, first elevator linkage 240*a* is translated down, forcing down a first end while raising an opposite, second end of second elevator linkage 240*b*, and thereby, translating third elevator linkage 240*c* upwards. This configuration is shown in FIG. 4B. Additionally, protrusion 145 is collinear with center longitudinal axis 21 such that the center longitudinal axis 21 intersects at least a portion of protrusion 145 and the center longitudinal axis 21 is perpendicular to axis 19.

The measurements of elevator linkages 240*a*, 240*b*, 240*c* may differ slightly, as well, in order to maximize the mechanical advantage of the subassembly or accomplish a desired configuration. While the measurements associated with lever 107 relative to axis 19 and a proximal portion of first elevator linkage 240*a* relative to axis 19 may be similar to the measurements described above with respect to the embodiment depicted in FIGS. 3A-3D, modifications may be made to accommodate the desired configuration. For example, the length of first elevator linkage 240*a* may be approximately about 40 mm, the length of second elevator linkage 240*b* may be approximately about 22 mm in length, and the length of third elevator linkage 240*c* may be approximately about 23.5 mm in length. The aforementioned exemplary lengths may accomplish a mechanical advantage of 2.5 within box E and a mechanical advantage of 1.07 within box F. It may also be understood that other lengths or measurements for the elevator lever 107 and one or more of the elevator linkages 240*a*, 240*b*, 240*c* may be utilized to accomplish a desired mechanical advantage or alternative configuration. For example, the lengths of elevator linkages 240*a*, 240*b*, 240*c* may be increased or decreased, if desired. Similarly to the method described above, in use, an operator may insert insertion portion 108 into a body lumen of a subject, and distal tip 119 may be navigated to a procedure site in the body lumen. The operator may insert a tool (not shown) into port 103, and pass the tool through shaft 128 via a working channel to distal tip 119. The tool may exit the working channel at distal tip 119. The user may use elevator control lever 107 to raise elevator 124 and angle the tool toward a desired location (e.g., a papilla of the pancreatico-biliary tract). The user may use the tool to perform a medical procedure.

In the arrangements discussed above with respect to FIGS. 3A-3D and 4A-4C, it may be understood that the elevator linkages 140*a*, 140*b*, 140*c*, 240*a*, 240*b*, and 240*c* may be comprised of a variety of biocompatible materials. This may include, stainless steel, polycarbonate, titanium, etc. Additionally, the shape of the elevator linkages 140*a*, 140*b*, 140*c*, 240*a*, 240*b*, and 240*c* may vary depending on the desired application. For example, the elevator linkages 140*a*, 140*b*, 140*c*, 240*a*, 240*b*, 240*c* may be curved to avoid interference between any components housed within the handle. Additionally, a variety of shapes may be utilized to further enable a better mechanical advantage. For example, the elevator linkages 140*a*, 140*b*, 140*c*, 240*a*, 240*b*, 240*c* may be S-shaped, C-shaped, or otherwise configured to further enable a mechanical advantage for the user.

One advantage of the disclosed embodiments includes the reduction of forces, or torque, on the system. For example, the force, or torque, necessary to manipulate a variety of tools may be reduced approximately 0.1-50% as a result of the arrangements discussed above with respect to FIGS. 3A-3D and 4A-4C. This is due to the increased mechanical advantage within the link mechanism assemblies.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A linkage assembly for a medical device, comprising:

a control lever;

a rotatable member rotatable about a first axis;

a slider having a longitudinal axis; and a plurality of linkages including a first linkage, a second linkage, and a third linkage; wherein:

the first linkage includes a first end coupled to the rotatable member and a second, opposite end coupled to a first end of the second linkage; and the second linkage includes the first end coupled to the second end of the first linkage and a second, opposite end coupled to a first end of the third linkage, wherein the second linkage is rotatable about a second axis parallel with the first axis;

wherein a second end of the third linkage translates along a third axis, wherein the second axis is offset from the third axis, wherein the third axis intersects the first axis, and wherein the longitudinal axis extends along the third axis, wherein the slider is connected to the second end of the third linkage.

2. The linkage assembly of claim 1, wherein, in a configuration in which the second linkage extends perpendicular to the longitudinal axis of the slider, the first end of the second linkage is a right-hand end of the second linkage when viewed from above.

3. The linkage assembly of claim 1, wherein, in a configuration in which the second linkage extends perpendicular to the longitudinal axis of the slider, the first end of the second linkage is a left-hand end of the second linkage when viewed from above.

4. The linkage assembly of claim 1, wherein the slider is operatively coupled to a control wire extending distally to an elevator, and wherein the slider moves within a track.

5. The linkage assembly of claim 4, wherein manipulation of the control lever is configured to result in manipulation of the elevator so as to adjust an orientation of a tool extending through the elevator.

6. The linkage assembly of claim 1, wherein at least one of the plurality of linkages is curved.

7. The linkage assembly of claim 1, wherein the second linkage pivots about a fixed protrusion extending along the second axis.

8. The linkage assembly of claim 7, wherein the second linkage is eccentrically mounted to the fixed protrusion such that a first length of the second linkage extending from the first end of the second linkage to the fixed protrusion is different than a second length of the second linkage extending from the fixed protrusion to the second end of the second linkage.

9. The linkage assembly of claim 7, wherein the fixed protrusion is offset from the longitudinal axis of the slider.

10. The linkage assembly of claim 1, wherein (i) the control lever, rotatable member, and first linkage form a second-class lever assembly, and (ii) the first linkage, second linkage, and third linkage form a first-class lever assembly.

11. The linkage assembly of claim 1, wherein the first linkage is coupled to an intermediary component, wherein the intermediary component is coupled to the rotatable member.

12. The linkage assembly of claim 4, wherein a proximal portion of the control wire further comprises a hypotube.

13. The linkage assembly of claim 1, wherein the plurality of linkages are configured in a Z-formation.

14. A linkage assembly for a medical device, the linkage assembly comprising:

a rotatable member configured to rotate about a first rotational axis;

a slider movable along a range of motion extending from a most retracted position of the slider to a maximum advancement of the slider; and a series of elevator linkages rotatably coupled to the rotatable member at a first end of the series and rotatably coupled to the slider on a second end of the series, wherein:

(i) at least one elevator linkage of the series of elevator linkages is rotatable about a second rotational axis different than and offset from the first rotational axis, (ii) movement of the slider along a range of motion results in movement of an elevator coupled to the slider via a control wire, and (iii) the slider translates along a third axis that intersects the first rotational axis.

15. The linkage assembly of claim 14, wherein a proximal portion of the control wire further comprises a hypotube.

16. The linkage assembly of claim 14, wherein the second rotational axis is perpendicular to a longitudinal axis extending longitudinally through the slider.

17. A linkage assembly for a medical device, the linkage assembly comprising:

a rotatable member configured to rotate about a first rotational axis;

a slider;

a plurality of elevator linkages; and an elevator assembly, wherein the plurality of elevator linkages form a plurality of levers to manipulate the elevator assembly, wherein:

the plurality of levers include (i) a second-class lever and (ii) a first-class lever connected to the second-class lever, and the elevator assembly is connected to the first-class lever; and in a first, proximalmost configuration of the rotatable member, the slider is in a distalmost position, and wherein, in a second, distalmost configuration of the rotatable member, the slider is in a proximalmost position, wherein at least one elevator linkage of the plurality of elevator linkages is rotatable about a second rotational axis different than and offset from the first rotational axis, and wherein the slider translates along an axis that intersects the first rotational axis.

18. The linkage assembly of claim 17, wherein the slider is operatively coupled to a control wire extending distally to an elevator, wherein, in the first configuration of the rotatable member, the elevator is in a closed position, and wherein, in the second configuration of the rotatable member, the elevator is in an open position.

* * * * *